United States Patent [19]

Gölander et al.

[11] Patent Number: 4,840,851

[45] Date of Patent: Jun. 20, 1989

[54] SURFACE COATED ARTICLE, PROCESS AND MEANS FOR THE PREPARATION THEREOF AND USE THEREOF

[75] Inventors: Carl G. Gölander, Stockholm; Erik S. Jönsson, Nässjö; Todorka G. Vladkova, Sofia, all of Sweden

[73] Assignee: Ytkemiska Institutet, Stockholm, Sweden

[21] Appl. No.: 862,504

[22] PCT Filed: Sep. 27, 1985

[86] PCT No.: PCT/SE85/00376

§ 371 Date: May 9, 1986

§ 102(e) Date: May 9, 1986

[87] PCT Pub. No.: WO86/02087

PCT Pub. Date: Apr. 10, 1986

[30] Foreign Application Priority Data

Sep. 28, 1984 [SE] Sweden .............................. 84048669

[51] Int. Cl.$^4$ .......................................... B32B 27/32
[52] U.S. Cl. ..................................... 428/523; 427/44; 427/307; 427/393.4; 427/385.5; 427/393.5; 428/500; 428/516
[58] Field of Search ...................... 427/393.4, 44, 307, 427/385.5, 393.5; 428/394, 395, 522, 523

[56] References Cited

U.S. PATENT DOCUMENTS

| | | | |
|---|---|---|---|
| 3,925,589 | 12/1975 | Sturwold et al. | 428/395 |
| 3,959,559 | 5/1976 | Kimoto et al. | 428/395 |
| 3,959,560 | 5/1976 | Sturwold et al. | 428/395 |
| 4,065,598 | 12/1977 | Takahashi et al. | 428/395 |
| 4,110,227 | 8/1978 | Newkirk et al. | 428/395 |
| 4,391,686 | 7/1983 | Miller et al. | 522/13 |
| 4,422,914 | 12/1983 | Tsao et al. | 525/920 |
| 4,537,922 | 8/1985 | Chang et al. | 428/523 |

FOREIGN PATENT DOCUMENTS 0057906 8/1982 European Pat. Off. .
149313 11/1980 Japan .

Primary Examiner—George F. Lesmes
Assistant Examiner—J. B. Monroe
Attorney, Agent, or Firm—Burns, Doane, Swecker & Mathis

[57] ABSTRACT

A surface coated article comprising a substrate with a cured polyethylene oxide-based coating thereupon. The essential features of the article are that the coating essentially consists of polyethylene oxide chains, with one free end and one end that has been cross-linked to other chains via a special cross-linking agent, that the cross-linking has been performed by radiation, and that the substrate has been swollen prior to cross-linking. The article can be prepared by applying to the substrate a solution containing the polyethylene oxide, the cross-linking agent, a swelling solvent and optionally a radical initiator, evaporating the solvent and cross-linking the coating by radiation curing. A suitable coating composition comprises per mole of the polyethylene oxide, 0.1–10 moles of the cross-linking agent, 0–500 moles of the solvent and optionally 0.0001–0.5 moles of the radical initiator.

The article is especially useful within the biomedical field.

29 Claims, No Drawings

SURFACE COATED ARTICLE, PROCESS AND MEANS FOR THE PREPARATION THEREOF AND USE THEREOF

TECHNICAL FIELD

The present invention is within the field of surface coating of a substrate, for instance a polymeric substrate, with a polymeric coating containing ethylene oxide units as primary structural units thereof. The new surface coating according to the invention imparts to the substrate outstanding properties which make it possible to utilize the surface coated articles obtained in novel applications as compared to previously known surface coated articles in this field. More specifically the invention relates to a surface coated article comprising a substrate with a curved polyethylene oxide-based coating thereupon, to a special process for the preparation of such a surface coated article, to a special coating composition for the preparation of said surface coated article and to use of the article as an antifouling or antistatic article or as an article with friction-reducing properties. A new, very interesting application of the article according to the invention is within the biomedical field, which is primarily due to the protein-repellent properties of the surface coating as will be described more in detail below.

BACKGROUND TO THE INVENTION

DT-PS No. 10 28 524 discloses a method of coating or impregnating textiles with a coating of polyalkylene oxide and the use of said coating as an antistatic, soil-repellent and water absorbing coating. A similar method is disclosed in DT-AS No. 22 39 592, which is specifically directed to a method of improving the stability of the coating by adding a cationic antistatic agent in the form of a reactive alkyl ethylene-urea and by performing the curing operation at elevated temperatures in the presence of moisture as a catalyst. According to both these references the preferred method for obtaining a cured coating seems to be the use of a polyalkylene oxide having at least two unsaturated groups in the form of acrylic, methacrylic and/or vinyl groups at the ends of the molecule or in side chains which groups are crosslinked by means of thermally activated initiators at elevated temperatures. Furthermore, these previously known methods require several process steps. It is true that DT-AS No. 22 39 592 mentions as an alternative the use of a mixture of a polyalkylene glycol with a polymerizable vinyl group in one end thereof and a vinyl monomer with at least two vinyl groups, but said alternative is in no way disclosed as any preferred alternative. Furthermore, said German citation neither discloses nor suggests the essential combination of features necessary according to the present invention or even less the outstanding combination of properties obtained by the present invention. Finally, no stabilization treatment is required in connection with the present invention as is required according to DT-AS No. 22 39 592.

Thus, as will be described more in detail below the present invention relates merely to polyethylene oxide as a coating material, which means essential advantages as compared to the use of other polyalkylene oxides, primarily thanks to the structural compatibility between the ethylene oxide units and the water molecules. However, the major difference relative to the prior art is not the use of polyethylene oxide per se but rather the following combination of features: the presence of ethylenically unsaturated groups at one end of the polyethylene oxide chains only, the way of accomplishing the cross-linking of the polyethylene oxide chains to obtain a stable coating on the substrate to be coated, viz. by radiation curing, and the swelling of the substrate prior to cross-linking. These major differences relative to the prior art impart to the manufactured article a unique structure of densely packed non-modified polyethylene oxide chains pendant from the substrate as well as a firm anchoring of the coating to the substrate.

As to the radiation curing this is a curing technique known per se, as is disclosed e.g. in EP, No. A1, 0 057 906. However, as was mentioned above the present invention is based on a combination of features, of which radiation curing is one only, giving results which are not in any way disclosed or suggested in the prior art.

SE Patent Application Ser.No. 8202524-8 discloses a method of applying to a polymeric substrate a hydrophilic coating of polyethylene oxide and its use in medical articles to be inserted into the human body. The polyethylene oxide is applied to the surface by swelling and curing at elevated temperature and in the presence of steam. Said known method differs from the present invention in that there are no unsaturated groups in the polyethylene oxide and that the cross-linking reactions are accomplished by means of a compound containing at least two non-reacted isocyanate groups and in the presence of a catalyst. A major drawback with this known method and with other prior art not utilizing the polyethylene oxide chain structure used according to the preesnt invention is, however, that during the cross-linking reaction the polyethylene oxide chains form loops at several reaction sites which means a poor degree of coating and an article that is less useful for practical purposes. This drawback is definitely eliminated by the present invention in that the structures of the reactions do not enable the formation of such loops. Furthermore, the process according to the present invention is much simpler than the method disclosed in the Swedish citation, as said method comprises several lengthy steps.

In connection with the prior art it should also be noted that the water-binding ability of polyethylene oxide is known per se and that said ability is utilized e.g. when impregnating wood to prevent dessication and the formation of cracks. Polyethylene oxide is also utilized when impregnating synthetic materials to impart antistatic properties thereto and in nonionic dispersants which adsorb and hydrophilize the surfaces of those particles and drops to be dispersed.

DISCLOSURE OF THE INVENTION

According to one aspect of the invention there is provided a surface coated article comprising a substrate and a cured polyethylene oxide-based coating thereupon. The essential features of said article are that:

(A) the coating consists essentially of polyethylene oxide chains, each of which has one end that is unmodified, free and pendant from said substrate and another that has been cross-linked, via one or more, preferably one, radiation curable, ethylenically unsaturated group(s) as part of said polyethylene oxide chain, to other chains by a cross-linking agent with two or more, preferably two or three, radiation curable, ethylenically unsaturated groups reactive with the ethylenically unsaturated groups of the polyethylene oxide chains, (B) the cross-linking operation has been performed by means of radiation, and (C) the substrate has been swollen prior to said cross-linking operation, the productions between polyethylene oxide and cross-linking agent being such that an adherent, cured coating is obtained.

The structure of the coating as well as the reactants to be utilized when preparing the coating will be described more in detail below but already here it should be noticed that the unique structure of the article, especially a very high surface concentration of freely movable polyethylene oxide chains, makes it useful especially as a protein-repellent article.

According to a second aspect of the invention there is provided a process for the preparation of a surface coated article of the above-mentioned type which process comprises applying to the substrate a solution containing (a) a polyethylene oxide having chains, each of which has one end that is free and unmodified and another that is cross-linkable, via one or more, preferably one, radiation curable, ethylenically unsaturated group(s) as part of said polyethylene oxide chain, to other chains, (b) a cross-linking agent with two or more, preferably two or three, radiation curable, ethylenically unsaturated groups reactive with the ethylenically unsaturated groups of the polyethylene oxide chains, (c) a solvent for said polyethylene oxide and said cross-linking agent, said solvent also being a swelling solvent for the substrate, and optionally (d) a radiation radical initiator; allowing said solvent to act on the substrate for a sufficient period of time to swell said substrate; evaporating said solvent to the formation of a coating on the substrate; and cross-linking said coating by means of radiation, the radical initiator being added separately if not already present in first-mentioned solution.

According to a third aspect of the invention there is provided a coating composition for the preparation of the surface coated article mentioned above or for use in the above-mentioned process, which coating composition comprises:

(a) a polyethylene oxide having chains, each of which has one end that is free and unmodified and another that is cross-linkable, via one or more, preferably one, radiation curable, ethylenically unsaturated group(s) as part of said polyethylene oxide chain, to other chains, and per mole of said polyethylene oxide, (b) a cross-linking agent with two or more, preferably two or three, radiation curable, ethylenically unsaturated groups reactive with the ethylenically unsaturated groups of the polyethylene oxide chains, the molar amount of said cross-linking agent being 0.1-10, preferably 0.3-3, moles thereof in the case when said cross-linking agent does not contain any significant portion of ethylene oxide units, and 0.02-50 moles thereof when it contains such ethylene oxide units, (c) 0-500, preferably 50-150, moles of a solvent for said polyethylene oxide and said cross-linking agent, said solvent also being a swelling solvent for the substrate, and (d) 0.0001-0.05, preferably 0.001-0.01, moles of a radiation radical initiator.

Accoding to a fourth aspect of the invention there are provided uses of the above-mentioned article, said uses in general terms being defined as an antifouling, biocompatible or antistatic article or as an article with friction-reducing properties. Specific uses within these general definitions will be described below.

Each and every component or reactant that is utilized according to the invention has a unique function and by optimizing these functions the coating can be tailored for almost any substrate surface and use. This in turn means that the invention is applicable to the coating of any substrate, e.g. a polymeric material, glass, metals, etc. However, since widely used polymeric materials are often of the nonpolar type which is not easily coated in a stable way, the invention is especially interesting in connection with such substrates.

A more detailed description of the functions referred to above will be given below.

THE POLYETHYLENE OXIDE

An essential feature of the polyethylene oxide to be used according to the invention is that generally each chain thereof has one end representing an unmodified polyethylene oxide terminal group, while the other end of said chain has at least one radiation curable ethylenically unsaturated group. That is, in the curing operation merely one end of the polyethylene oxide chain contains reactive group(s) capable of participating in the cross-linking reaction, while the other end of the chain does not contain any group that participates in such a cross-linking reaction. Preferably the reactive end of the chain contains one single ethylenically unsaturated group only, but within the scope of the invention are also such cases where two or three or even more unsaturated groups are present, the proviso being that such reactive groups are positioned so close to the end of the chain that no essential loops may be formed during the curing operation. In other words there should be always be present a free movable polyethylene oxide chain pendant from the substrate surface and directing itself towards an aqueous phase in contact with the coated article.

Examples of suitable ethylenically unsaturated groups are acrylic and methacrylic groups, but groups from any ethylenically unsaturated compound which can be polymerized or cross-linked by radiation radical initiation are within the scope of the invention. A preferred sub group of ethylenically unsaturated groups, including the above-mentioned acrylic and methacrylic groups, is polarized ethylenically unsaturated groups. Preferably, however, the unsaturated groups are derived from an ethylenically unsaturated carboxylic acid with a low molecular weight, preferably with an average molecular weight below 1000, especially below 200.

The term "unmodified" or similar in connection with the end of the polyethylene oxide which is pendant from the substrate should be understood in a broad sense. In other words the requisite according to the present invention is that said end does not contain any ethylenical unsaturation that takes part in the cross-linking reaction. Generally this means a conventionally etherified end of a polyethylene oxide. The other end, i.e. the reactive end, of the polyethylene oxide can be obtained for instance by reacting a chemically unmodified hydroxyl end of a polyethylene oxide by an esterification reaction with a compound containing the ethylenically unsaturated group(s). If desired, said compound may also contain different functional groups dependent on the final utility of the article to be manufactured. Anotehr preferable method of preparing the polyethylene oxide reactant according to the invention, however, is to start from a compound containing the ethylenically unsaturated group(s) and ethoxylating the same, which ethoxylation is performed in a manenr known per se. A major advantage of such a method is that the polyethylene oxide chains obtained represent a mixture of chains with a distribution of molecular weights within a desired range, e.g. the so-called Poisson distribution.

With reference to the length or molecular weight of the polyethylene oxide chains a preferable lower limit of the ethylene oxide units, to obtain the desired hydrophilicity and similar properties, is 10 and especially 30. As to the upper limit of the number of such units there is no strictly critical such limit, but generally it can be advisable not to exceed 500 ethylene oxide units, as this may cause crystallinity or other properties which may be non-advantageous for specific applications. An especially preferable upper limit as to ethylene oxide units is 200, which means that the most perferable range in this respect is 30-200.

THE CROSS-LINKING AGENT

As was mentioned above this reactant is an agent with two or more radiation curable ethylenically unsaturated groups reactive with the ethylenically unsaturated groups of the polyethylene oxide chains. This means that in general terms the ethylenically unsaturated groups are of the same nature as the corresponding groups of the polyethylene oxide chains, i.e. the preferred sub groups as well as the preferred specific groups are the same as were mentioned above in connection with the polyethylene oxide. Thus, interesting groups of the cross-linking agent are allylic, acrylic or methacrylic groups. Furthermore, said cross-linking agent is preferably a compound having a low molecular weight, which according to an especially preferble embodiment of the invention means an average molecular weight below 1000, especially below 300. Thus, the term compound should be read in a broad sense and includes polymers or oligomers as well as mixed polymers or oligomers. As was mentioned in connection with the polyethylene oxide said compound can also contain different functional groups if desired for any specific purpose. Thus, it may be chosen in dependency of the substrate to be coated to improve the adhesion or to improve the flexibility of the applied coating, etc.

According to anotehr interesting embodiment of the invention the cross-linking agent contains, in addition to ethylenically unsaturated groups, one or more polyethylene oxide chains containing 5-500, preferably 3-200, ethylene oxide units having a free, non-reacted end. Finally, it should be noted that the most preferable number of ethylenically unsaturated groups of the crosslinking agent is 2 or 3.

A specific example of preferable cross-linking agent is hexamethylenedioldiacrylate.

The polyethylene oxide and cross-linking reactants are of course used in such proportions or molar ratios that a cured adherent coating having the desired properties for the intended end use of the article is obtained. These ratios are difficult to generalize as they very much depend on the specific nature of the polyethylene oxide reactant and the cross-linking agent, respectively, but can be established by routine experiments in each single case now that the inventive idea has been disclosed. Thus, for instance, different molar ratios may be required whether the cross-linking agent contains ethylene units or not. However, some guidance in this respect is given below in connection with the special coating composition described below.

With reference to the cross-linking operation and the swelling of the substrate these essential features have been referred to in general terms above. More detailed information therabout will be given below in connection with the disclosure of the process according to the invention.

The essential features of the process according to the invention have been generally described above. As to the details concerning the polyethylene oxide and the cross-linking agent reference is made to the details above. With reference to the solvent, however, the following could be added.

The process according to the invention involves the use of a solvent that in addition to the desired dissolution, spreading and evaporation capacities also swells the substrate to be coated. This technique relates primarily to the case where a polymeric substrate is utilized and means that an improved anchoring effect can be obtained. Thus, by using a solvent having such a swelling capacity the subsequent cross-linking rection can cause bridges or cross-links which are more or less mechanically anchored to the swollen substrate.

The primary functions of the solvent are:

(1) The solvent should be capable of dissolving the polyethylene oxide and the cross-linking agent, (2) it should wet the surface of the substrate so as to obtain a homogenous spreading of the polyethylene oxide, (3) it should swell the substrate surface so as to obtain a mechanical anchoring of the polyethylene oxide to the substrate surface, and (4) it should have an evaporation rate such that the time will be sufficient for the substrate surface to be swollen and so that a homogenous and covering film is obtained (this is promoted by a slow evaporation of the solvent without any complete sorbtion of the polyethylene oxide into the polymer).

Generally a mixture of solvents is required to obtain the above-mentioned functions, which solvents must be compatible with each other, since otherwise another function is required, namely the ability of bringing about dissolution capacity. The solvent or solvent mixture to be used in a specific case is determined by routine experimentation. Factors to be considered in this respect are e.g. the substrate to be coated, the evaporation rate and the environmental requirements. As an example it can be mentioned that for polyvinylchloride a suitable mixture is a mixture in equal parts of tetrahydrofurane (swells PVC), toluene and ethanol (dissolves polyethylene oxide and wets the surface and gives a suitable evaporation rate).

In accordance with the invention the curing of the coating composition is accomplished by means of radiation initiated polymerization which is a rapid, easy and effective way of obtaining the desired results. Thus, the initiators to be used are initiators activated by radiation such a gamma-X rays, electron beams or ultra violet radiation. Ultra violet radiation activation is preferable and can be performed at ordinary room temperature which of course means great advantages as compared to the prior art. UV polymerization requires presence of a photo initiator, which can preferably be of the socalled photo phragmentating type, e.g. 2-hydroxy-2-propiophenone, two reactive radicals being formed directly when starting the radiation, or preferably of the H-abstraction type, radicals being generated via h-abstraction from an added tertiary amine (contains acidic α-hydrogens, for instance thioxanthone+trimethyl amine). As last-mentioned type of initiator may also abstract hydrogens to some extent from the polyethylene oxide as well as from a polymeric substrate, the adhesion to a polymeric substrate can be improved thereby through the formation of chemical bonds with the substrate, which means that this represents an especially preferable embodiment of the process according to the invention.

According to yet another especially preferable embodiment of the process the cross-linking operation is performed in two steps, viz.:

(i) a partial cross-linking in air for a short time to the formation of a polyethylene oxide gel, which is sparingly soluble in water but wherein the polyethylene oxide segments retain some movability; and (ii) a final curing of said gel in an aqueous phase whereby the polar polyethylene oxide segments orient themselves towards the aqueous phase. This means an essential advantage as compared to the prior art since the structure of the coating according to the invention is such that the polyethylene oxide chains will be high-ly concentrated to the surface of the manufactured article, i.e. essentially all chains will be directed towards the aqueous phase.

In practice the process according to the invention can be performed by roller-coating or spraying to the surface of the substrate or immersing the substrate into the solution containing the polyethylene oxide, the cross-linking agent and optionally also the radical initiator. Excess of solvent is then allowed to flow off and evaporate from the surface. Finally the dry or at least non-flowing coating is cured by radiation, for instance by passing the substrate with the applied coating thereupon past the radiation source on a conveyor.

Generally this means that the process according to the invention is performed in two major stages which are simple and rapid. As compared to the previously known methods this means significant advantages also as to operability and costs, i.e. in addition to the advantages obtained by the coated article per se.

The invention also relates to a special coating composition for the preparation of a surface coated article as described above or for use in the special process claimed. The proportions between the different ingredients of said special composition are as follows. Per mole of the polyethylene oxide there are used 0.1–10, preferably 0.3–3, moles of the cross-linking agent in the case when said cross-linking agent does not contain any significant portion of ethylene oxide units, and 0.02–50 moles of said cross-linking agent in the case when it contains such ethylene oxide units; 0–500, preferably 50–150, moles of the solvent; and optionally 0.0001–0.05, preferably 0.001–0.01, moles of the radiation radical initiator, Thus, in the case when no significant proportion of ethylene oxide units is present in the cross-linking agent the molar ratio of polyethylene oxide: cross-linking agent should generally be from 1:10 to 10:1, but to obtain optimum properties in this case said ratio is preferably from 1:3 to 3:1. Especially preferable is a molar ratio at or near 1:1 for lower molecular weight polyethylene oxides, said ratio being closer to 1:3 the higher the molecular weight of the polyethylene oxide is.

For cross-linking agents containing ethylene oxide units the variations as to molar ratios are greater or more versatile as part of desirable properties ascribable to ethylene oxide units can be imparted to the article also by the cross-linking agent. Therefore, the general limits as concerns the above-mentioned ratio can be expressed as 1:50 and 50:1, respectively, a more narrow general range being difficult to state depending on the (very interesting) versatility of this embodiment of the invention. However, in some cases the above-mentioned ranges of 1:10 to 10:1 and 1:3 to 3:1 are applicable also to this case.

As was mentioned above the invention finally relates to special uses of the article. Said uses can generally be expressed as an antifouling or antistatic article or as an article with friction-reducing properties. More specifically, it has been found that the article according to the invention possesses excellent protein adsorption-preventing properties, which open great possibilities within the biomaterial field, especially the biomedical field. The biocompatibility is especially pronounced for polyoxyethylene chains with at least 10 or more, preferably at least 25 or 30 ethylene oxide units.

Furthermore, the surface coating according to the invention makes hydrophobic surfaces completely hydrophilic and water-wetting and facilitates the cleaning of contaminated areas. It also prevents a static charging of the substrate surface, is oil-repellent as well as particle-repellent. Another important property that can be utilized for special applications is the property to reduce friction between surfaces.

Medical uses for which the article according to the invention can be expected to be applicable are for instance:

tissue-compatible surfaces to be used within the human body, e.g. in vessel and bone prostheses to prevent rejection reactions;

blood-compatible surfaces to prevent blood coagulation and protein depositions, e.g. when utilizing catheters and in extracorporal circulation, such as oxygenators and artificial kidneys;

dressings for the adsorption of tissue liquids.

If the composition is impregnated with iodine $I_2KI$ there is also obtained a disinfecting and wound healing effect;

applications where bacterial growth on surfaces (antibacterial effect) is prevented, are e.g. in connection with urinary catheters and in contraceptives as a sperm-killing coating.

In connection with the medical uses of the article according to the invention the radiation curing offers great advantages as it means that at the same time a sterilization of the product is obtained.

EXAMPLES

The invention will now be described more in detail by means of the following non-limiting examples of represenattive embodiments of the invention.

EXAMPLE 1

Monoethyl-etherified polyethylene glycol (PEG) with a molecular weight of 550 was monoacrylated with acrylic acid. After evaporation to obtain a product designated PEG-A-550 there were added to said product 0.02 moles of hexamethylene diol diacrylate (HDDA) (difunctional cross-linking agent), 0.0002 moles of 2-hydroxy-2-propiophenone (photoinitiator) and a solvent mixture consisting of 1.5 moles of ethanol, 0.75 moles of toluene and 1.0 mole fo tetrahydrofurane (THF).

Three different samples were prepared, viz.: Sample A containing 0.005 moles of PEG-A-550 Sample B containing 0.02 moles of the same compound, and Sample C containing 0.4 moles of said compound.

Each of said solutions were dropped onto a PVC plate, and the solvent was allowed to evapoorate, whereupon the applied coating was cured at a speed of 6 m/min in a UV cure from Primare, U.S.A., which contains two Hg lamps giving a power of 100 W/cm.

The samples were rinsed with water for 60 seconds. Only sample B gives a completely hydrophilic, water-wetting surface.

EXAMPLE 2

To a 0.02 moles of PEG-A-1900 there were added 0.02 moles of HDDA and 0.0002 moles of 2-hydroxy-2-propio-phenone. As a solvent there was used pure 0.2 moles of p-xylene (swells PE).

This solution (D) as well as solution (B) from Example 1 (prepared with PEG-A-1900 instead of PEG-A-550) were applied in a thin layer onto a polyethylene surface. The solvent was allowed to evaporate and the coating was cured as in Example 1.

The products obtained were rinsed in water for 60 seconds. Only product D was completely hydrophilic, Coating B scaled off with time.

The product was then dipped into a beaker containing heavy fuel oil. On both samples a black oily film was observed. If the samples were re-immersed into water the oil was scaled off from coating (D), which became completely clean from oil. Sample (B) was still covered by oil and could not be cleaned by rinsing in water.

EXAMPLE 3

Coating compositions prepared according to (B) in Example 1 and containing PEG-A-550, PEG-A-1900 and PEG-A-5000, respectively, were evaporation coated onto a PVC foil and cured in a UV-cure according to Example 1.

All samples were exposed for 6 hours to 1% bovine serum albumine (BSA), dissolved in a physiologic sodium chloride solution, whereupon the surfaces were rinsed in a clean physiological sodium salt solution for 60 minutes. The samples were dried and surface analyzed by means of electrone microscopy for chemical analysis=ESCA with relation to protein nitrogen.

For all PEG:s the protein adsorption was reduced as compared to untreated PVC. The adhered amount of protein is reduced with increasing molecular weight of the PEG in the following way:

| Coating | Mole % of N in the surface |
| --- | --- |
| Untreated PVC | 5 |
| PEG-A-550 | 2 |
| PEG-A-1900 | 0.9 |
| PEG-A-5000 | <0.5 |

EXAMPLE 4

A coating composition prepared according to (B) of Example 1 above but with PEG-A-1900 was applied to two plates of stainless steel which had previously been provided with a thin PVC film by evaporating a 0.5% PVC solution in THF on the steel plate. The coating composition was allowed to dry in air, and then one of the samples was cured in a normal way with one stage in air, while the other plate was cured in two stages: firstly a partial and very rapid (<0.5 m/min), exposure in UV-cure in air, and secondly covering of the coating composition by a film of water below which final curing was performed at a speed of 5 m/min in a UV-cure.

The samples were exposed to 1% of BSA with subsequent rinsings as in Example 3.

The protein contents were determined by means of

| Type of cure | Mole % of N in the surface |
| --- | --- |
| Cure in one stage | 0.9 |
| Cure in two stages | <0.5 |

The proportions of PEG (in the form of -$CH_2O$-carbon) in the surface was analyzed by means of ESCA with the following results:

| Type of cure | Mole % of PEG |
| --- | --- |
| Cure in one stage | 60 |
| Cure in two stages | >90 |

EXAMPLE 5

Trimethylol propane (TMP) that had been ethoxylated with 20 ethylene oxide units per TMP was diacrylated by charging 2 moles of acrylic acid per mole of TMP.

To 0.003 moles of the dried product (TMP-$(EO)_{20}$-A) there were added.

0.0001 moles of 2-hydroxy-2-propiophenone
0.78 moles of ethanol
0.50 moles of toluene
0.25 moles of TMF The coating composition was applied to Plexiglas ® (PMMA) and the film was cured in accordance with the two-stage process of Example 4. One untreated and one treated PMMA plate were exposed to a power mixture of iron oxide ($Fe_2O_3$) and colloidal carbon (equal parts of each based on the weights) with shaking in a test chamber at a relative humidity of 70% for 15 minutes.

The untreated sample had a permanent red-black coating after said test, while the treated sample was completely free from particles when it was taken out from the chamber.

EXAMPLE 6

A silicon plate was provided with a PVC film by immersion into a 0.5% solution of PVC in THF. The plate was then coated with a film having the following composition:

0.02 moles of PEG-A-5000
0.04 moles of trimethylol propane triacrylate (TMPTA)
0.0002 moles of 2-hydroxy-2-propiophenone
2 moles of ethanol
2 moles of toluene
2 moles of THF The films were spun onto a rotating plate at 100 rpm dried and cured in one single stage. The protein adsorption was measured by means of ellipsometry. The following results were obtained:

| Substrate | Thickness (Å) |
| --- | --- |
| Silicon-PVC | 20–30 Å |
| Silicon-PVC-PEG-A-500 | <2 Å |

EXAMPLE 7

Cell and platelet adhesion

Equimolar amounts (0.01 mol) of monoacrylated PEG 1900 and hexanediol diacrylate were dissolved in a mixture of toluene-cyclohexanone-ethanol, one part by weight of each, and diluted to a final solids content of 0.5% by weight.

The solution was applied to (a) PVC films and PMMA sheets, each with the dimension of 3×3 cm, by using a spiral rod applicator giving a thickness of 1 μm.

(b) The insides (lumens) of nearly transparent PE tubings with a length of 1 m and an inner diameter of 2 mm were treated by pouring the solution through the lumen with a pipette. Prior to application of the PEG film the PE tubings were made hydrophilic by exposure for two minutes to conc. sulphuric acid containing 2 g/l of potassium permanganate followed by thorough rinsing in water.

For both groups of substrates the solvents were evaporated to dryness before curing. All items were cured for 15 minutes in a Minicure instrument. Especially the inside of the tubings need to be cured for a long time since light scattering and absorbance occur in the tubing material.

Group (a) substrates which were first ethanol sterilized were exposed to 75 ml of a fibroblast cell culture containing 1 million of cells per ml. The suspension were allowed to sediment onto the substrates for one hour and subsequently the substrates were transferred to a solution of sensefetal calf serum and incubated at 37° C. up to 48 hours. The surfaces were then visually inspected and photographed in a microscope. On non-treated PMMA a congruent cell layer was seen after 48 hours which completely covered the surface by forming a network of cell protruberances which adhered strongly to the surface. For PEG-treated PVC and PMMA only isolated cells were seen with a spherical shape indicating that these cells were intact and not growing on the surface. This test shows that in contrast to normal polymer substrates PEG-coated surfaces do not favour cell growth and show extremely low cell adhesion.

Group (b) treated tubings were tested in respect of platelet adhesion. The tubings were circulated with fresh human citrated blood for 20 minutes and then rinsed in a standardized way with saline. Eventually ATP (adenosine triphosphate) was extracted from the adhered platelets with a buffer solution and the amount of ATP was determined. The following results were obtained:

Untreated polyethylene $1500 \times 10^{-11}$ mmol ATP/cm$^2$

PEG acrylate treated polyethylene $13 \times 10^{-11}$ mmol ATP/cm$^2$

These results show that the substrate surface (polyethylene) was completely covered by a platelet repellant PEG-film.

EXAMPLE 8

Antistatic properties

Videoscreens were coated with a number of films according to Examples 1, 2 and 3.

Changes in the electrostatic field strength were measured with an electrostatic field strength meter of type Eltex Q 475/A,C.

The following experimental conditions were used. (a) The thickness of the PEG-acrylate coating was less than 5 μm. (b) The PEG-acrylate coatings were cured on a rotating disc using 4×300 W Osram ultra vitalux UV-lamps. (c) The video screen was operated for 1 hour. The video screen was switched off and the changes in electrostatic field strength were measured at a fixed distance of 30 cm from the screen surface as a function of time.

Results

| Screen | Time (minutes) | El.field strength (kV/m) |
|---|---|---|
| Ref uncoated | 0 | 30.0 |
| | 2 | 30.0 |
| | 4 | 30.0 |
| | 6 | 30.0 |
| | 8 | 30.0 |
| | 10 | 30.0 |
| | 12 | 30.0 |
| | 14 | 30.0 |
| | 16 | 30.0 |
| | 18 | 30.0 |
| | 20 | 30.0 |
| coating: PEG 1900A/HDDA 1:10 | 0 | 30.0 |
| | 2 | 25.0 |
| | 4 | 25.0 |
| | 6 | 25.0 |
| | 8 | 25.0 |
| | 10 | 25.0 |
| | 12 | 25.0 |
| | 14 | 25.0 |
| | 16 | 25.0 |
| | 18 | 25.0 |
| | 20 | 25.5 |
| coating: PEG 1900A/HDDA 1:5 | 0 | 17.0 |
| | 2 | 12.0 |
| | 4 | 10.0 |
| | 6 | 8.8 |
| | 8 | 7.5 |
| | 10 | 6.5 |
| | 12 | 5.5 |
| | 14 | 5.0 |
| | 16 | 4.5 |
| | 18 | 4.0 |
| | 20 | 3.5 |
| coating: PEG 5000A/HDDA 1.5 | 0 | 20.0 |
| | 2 | 13.0 |
| | 4 | 9.0 |
| | 6 | 6.5 |
| | 8 | 5.0 |
| | 10 | 4.0 |
| | 12 | 3.0 |
| | 14 | 2.5 |
| | 16 | 2.0 |
| | 18 | 1.5 |
| | 20 | 1.0 |
| | 22 | 1.0 |
| coating: PEG 5000A/TMP(EO)$_{20}$A 1:3 | 0 | 25.00 |
| | 2 | 5.50 |
| | 4 | 2.50 |
| | 6 | 1.40 |
| | 8 | 1.10 |
| | 10 | 1.00 |
| | 12 | 1.00 |
| | 14 | 1.00 |
| | 16 | 0.95 |
| | 18 | 0.97 |
| | 20 | 0.97 |

This test clearly shows that PEG-acrylate films drastically reduce the electrical field strength outside the screen surface and therefore are effective as antistatic coatings.

We claim:

1. A surface coated article comprising (i) a substrate with (ii) a cured polyethylene oxidebased coating thereupon consisting essentially of polyethylene oxide chains, each of which has one end that is unmodifed, free and pendant from said substrate and another that has been crosslinked, via one or more radiation curable, ethylenically unsaturated group(s) as part of said polyethylene oxide chain, to other chains by a cross-linking agent with two or more radiation curable, ethylenically unsaturated groups reactive with the ethylenically unsaturated groups of the polyethylene oxide chains, the surface coated article being produced by the process of (i) cross-linking by means of radiation, and (ii) swelling the substrate prior to said cross-linking operation, the proportions between polyethylene oxide and crosslinking agent being such that an adherent, cured coating is obtained.

2. An article according to claim 1 wherein the ethylenically unsaturated groups of the polyethylene oxide chains as well as of the cross-linking agent are groups with a polarized ethylenical unsaturation.

3. An article according to claim 2 wherein the polyethylene oxide chains contain at least 10 ethylene oxide units each.

4. An article according to claim 3 wherein said polyethylene oxide chains contain at least 30 ethylene oxide units each.

5. An article according to claim 2 wherein the groups with a polarized ethylenical unsaturation are acrylate or methacrylate groups.

6. An article according to claim 1 wherein the unsaturated groups of the polyethylene oxide chains are derived from an ethylenically unsaturated carboxylic acid having an average molecular weight below 1000.

7. An article according to claim 6 wherein the low molecular ethylenically unsaturated carboxylic acid has an average molecular weight below 200.

8. An article according to claim 6 wherein the polyethylene oxide chains are derived from acrylic or methacrylic groups.

9. An article according to claim 1 wherein the cross-linking agent has an average molecular weight below 1000.

10. An article according to claim 9 wherein the cross-linking agent has a molecular weight below 300.

11. An article according to claim 9 wherein the cross-linking agent has allylic, acrylic or methacrylic groups.

12. An article according to claim 9 wherein the cross-linking agent is hexamethylenediol diacrylate.

13. An article according to claim 1 wherein the polyethylene oxide chains contain at least 10 ethylene oxide units each.

14. An article according to claim 13 wherein the polyethylene oxide chains contain at least 30 ethylene oxide units each.

15. An article according to claim 1 wherein the polyethylene oxide chains contain at most 500 ethylene oxide units each.

16. An article according to claim 15 wherein the polyethylene oxide chains contain at most 200 ethylene oxide units each.

17. An article according to claim 1 wherein the cross-linking agent contains, in addition to the ethylenically unsaturated groups, one or more polyethylene oxide chains containing 5-500 ethylene oxide units having a free, nonreacted end.

18. An article according to claim 17 wherein the polyethylene oxide chains contain 30-200 ethylene oxide units having a free, non-reacted end.

19. An article according to claim 1 wherein the swollen substrate has been obtained by means of a swelling solvent.

20. An article according to claim 1 wherein the radiation is UV radiation.

21. An article according to claim 1 wherein the radiation operation has been performed at or near room temperature.

22. An article according to claim 1 wherein each end which has been crosslinked, of said polyethylene oxide chains, is cross-linked via one radiation curable, ethylenically unsaturated group.

23. An article according to claim 1 wherein said cross-linking agent has two or three radiation curable ethylenically unsaturated groups reactive with the ethylenically unsaturated groups of the polyethylene oxide groups.

24. An article according to claim 1 wherein the substrate is a polymer and wherein the cross-linking step (i) is carried out in the presence of an initiator capable of abstracting hydrogens from the polyethylene oxide and from the polymeric substrate to form chemical bonds between the substrate and the polyethylene oxide.

25. A process for the preparation of a surface coated article according to claim 1 comprising applying to the substrate a solution containing (a) a polyethylene oxide having chains, each of which has one end that is free and unmodified and another that is cross-linkable, via one or more, preferably one, radiation curable, ethylenically unsaturated group(s) as part of said polyethylene oxide chain, to other chains, (b) a cross-linking agent with two or more, preferably two or three, radiation curable, ethylenically unsaturated groups reactive with the ethylenically unsaturated groups of the polyethylene oxide chains, and (c) a solvent for said polyethylene oxide and said cross-linking agent, said solvent also being a swelling solvent for the substrate; allowing said solvent to act on the substrate for a sufficient period of time to swell said substrate; evaporating said solvent to the formation of a coating on the substrate; and cross-linking said coating by means of radiation.

26. The process according to claim 25 wherein the solution further contains (d) a radiation radical initiator which is added separately if not already present in first-mentioned solution.

27. A process according to claim 26 further comprising using a radiation radical initiator of the H-abstracting type, whereby adhesion to a polymeric substrate can be improved by an anchoring effect.

28. The process according to claim 27 wherein the radical initiator of the H-abstracting type is benzophenone or thioxanthone.

29. A process according to claim 25 further comprising performing the radiation cross-linking operation in two steps, viz:
(i) a partial cross-linking in air for a short time to the formation of a polyethylene oxide gel, which is sparingly soluble in water but wherein the polyethylene oxide segments retain some movability; and
(ii) a final curing of said gel in water, whereby the polar polyethylene oxide segments orient themselves towards the water.

* * * * *